US 6,554,821 B2

(12) United States Patent
Stringer et al.

(10) Patent No.: US 6,554,821 B2
(45) Date of Patent: Apr. 29, 2003

(54) PERITONEAL WASTE BAG SUPPORT AND DRAINAGE DEVICE

(76) Inventors: Robert Stringer, 2 Narrows Rd. South #2E-1, Staten Island, NY (US) 10305; Jennifer Daupheny, 2 Narrows Rd. South #2E-1, Staten Island, NY (US) 10305

( * ) Notice: Subject to any disclaimer, the term of this patent is extended or adjusted under 35 U.S.C. 154(b) by 342 days.

(21) Appl. No.: 09/738,836

(22) Filed: Dec. 15, 2000

(65) Prior Publication Data
US 2002/0077608 A1 Jun. 20, 2002

(51) Int. Cl.$^7$ ................................. A61F 13/15
(52) U.S. Cl. ..................... 604/540; 604/322; 604/356
(58) Field of Search ..................... 604/317, 322, 604/323, 540, 541, 543, 544, 356, 327, 328, 332, 333, 334; 5/604, 605, 606, 607, 608

(56) References Cited

U.S. PATENT DOCUMENTS

| 759,084 | A | * | 5/1904 | Stahl ........................... 604/357 |
| 763,304 | A | * | 6/1904 | Meinecke et al. ........... 604/357 |
| 826,978 | A | * | 7/1906 | Whittington ................... 5/604 |
| 846,236 | A | * | 3/1907 | Noble ........................... 5/84.1 |
| 2,176,235 | A | * | 10/1939 | Woodard ..................... 128/227 |
| 2,664,573 | A | * | 1/1954 | Taylor ............................ 4/661 |
| 2,852,025 | A | * | 9/1958 | Wessels ....................... 128/227 |
| 3,231,901 | A | * | 2/1966 | Kennedy ......................... 4/110 |
| 3,598,124 | A | * | 8/1971 | Andersen et al. ........... 128/275 |
| 3,655,157 | A | | 4/1972 | Dalton ........................... 248/97 |
| 4,221,371 | A | * | 9/1980 | Kuphal ........................... 5/606 |
| 4,287,422 | A | * | 9/1981 | Kuphal et al. ............. 250/439 R |
| 4,414,968 | A | * | 11/1983 | Amin ........................... 128/853 |
| 4,645,497 | A | * | 2/1987 | Lowder ....................... 604/276 |
| 4,747,166 | A | * | 5/1988 | Kuntz ........................... 4/144.1 |
| 4,766,622 | A | | 8/1988 | Pacelli ............................ 4/661 |
| 4,889,300 | A | | 12/1989 | Gibson et al. ................. 248/97 |
| 4,936,836 | A | * | 6/1990 | Weickgenannt ............. 604/322 |
| 4,974,604 | A | * | 12/1990 | Morris ........................ 128/853 |
| 5,078,705 | A | * | 1/1992 | Edwards et al. ............ 604/322 |
| 5,176,667 | A | * | 1/1993 | DeBring ...................... 604/356 |
| 5,503,633 | A | | 4/1996 | Saunders et al. ............ 604/332 |
| 5,568,817 | A | * | 10/1996 | Harty .......................... 128/849 |
| 5,926,875 | A | * | 7/1999 | Okamoto et al. .............. 5/605 |
| 6,045,097 | A | | 4/2000 | Gaffar .......................... 248/95 |

FOREIGN PATENT DOCUMENTS

GB          2 206 274 A    *   1/1989   ........... A61F/5/449

* cited by examiner

Primary Examiner—Weilun Lo
Assistant Examiner—Michael G Bogart
(74) Attorney, Agent, or Firm—Goldstein & Lavas, P.C.

(57) ABSTRACT

A peritoneal waste bag support and drainage device having a pair of front legs, a pair of rear legs, and a flat horizontal table extending over the front and rear legs. The table has a front end, a rear end, a top surface, and a bottom surface. Each pair of legs has a main portion and a bottom sleeve. The main portion extends downward from the bottom surface of the table, while the bottom sleeve extends upward from the ground and envelopes the main portion of the legs. In order to adjust the length of the legs, the main portion is slid inside the corresponding bottom sleeve until the desired height to reached. When setting up the support device for drainage, in order to facilitate flow of fluid from a peritoneal waste bag, the front legs should be adjusted to a shorter height than the rear legs. Further, the device is collapsible in order to allow it be stored beside a toilet when not in use, or carried to various destinations when traveling.

1 Claim, 3 Drawing Sheets

PERITONEAL WASTE BAG SUPPORT AND DRAINAGE DEVICE

BACKGROUND OF THE INVENTION

The invention relates to a peritoneal waste bag support and drainage device. In particular, the invention is a collapsible table that supports and promotes the drainage of fluids from a peritoneal waste bag in an efficient and sanitary manner.

Healthy kidneys clean the blood by filtering out extra water and wastes. In addition they also produce hormones that aid in maintaining strong bones and healthy blood. In the event that a patient's kidneys fail to operate properly, his or her body holds the fluids in the blood. Thereafter, the blood pressure may rise and cause harmful wastes to build up in the body. Further, the body fails to produce an adequate level of red blood cells. In response, one needs to receive regular treatments to replace the work of the failed kidneys in order to remove waste products from the blood.

Artificial kidney machines and procedures have been developed that make use of dialysis to purify the blood of persons whose kidneys have ceased to function. Peritoneal dialysis, a procedure that replaces the work of one's kidneys, is becoming the most rapidly growing area of dialysis in the country today. This type of dialysis uses the lining of the abdomen, known as the peritoneal membrane, to filter the blood. It removes extra water, wastes, and chemicals from the body, without having to physically remove blood from the patient's body.

In peritoneal dialysis, the dialysis fluid, a cleaning solution called dialysate, is introduced into the abdominal cavity through a small, pliable tube, known as a catheter. This catheter is surgically inserted into the patient's abdomen, and serves to transport the dialysate to and from the peritoneal membrane. Fluid, wastes, and chemicals pass from tiny blood vessels in the abdominal peritoneal membrane into the dialysate. After several hours, the dialysate is drained from the abdomen, removing the wastes from the blood with it. The abdomen is then filled with fresh dialysate and the cleaning process begins again.

Many advantages of peritoneal dialysis have been recognized since the introduction of the procedure in the early 1980s. Besides reducing the amount of time needed to travel to and from a hospital or dialysis center, this type of dialysis promotes physical independence. Further, a patient is able to travel to any part of the world, as long as advance notification is given in order to have his or her solution shipped by the manufacturer to the destination. Besides the obvious advantages, peritoneal dialysis is also less obtrusive to one's body. This procedure promotes a general feeling of wellness since a blood pump is not necessary, and blood is not removed from the body. Moreover, access for this type of dialysis is obtained with a simple operation to the abdominal wall wherein a catheter is put in place.

Patients utilizing peritoneal dialysis are often faced with the task of lifting, carrying, and emptying the waste bag after drainage. Because of the amount of fluid that accumulates after several hours, the bag is quite heavy and cumbersome to transport. Further, it may take several minutes for the bag to drain, during which time one has to wait, holding the bag in order to ensure that it does not slip away from the toilet or sink.

Thus, there exists a need for a device which may aid one in emptying his or her peritoneal bag efficiently and in a sanitary manner. Such a device would provide a base to support the bag and aim the contents contained therein into the toilet or sink during drainage, without the need of a person to stand and hold same.

U.S. Pat. No. 4,766,622 to Pacelli discloses a peritoneal waste discharge system including a disinfectant storage chamber, a measuring chamber, a discharge cup, a peritoneal bag, and a conduit. All components are in selectable fluid contact with each other. While this system may serve to adequately disinfect the waste before discharge, it is cumbersome and may not be easily transported. Further, the construction demands that the unit be kept entacted in one's bathroom, in close proximity to the toilet.

U.S. Pat. No. 5,503,633 to Saunders et al. discloses a ostomy bag cleaning apparatus wherein a patient may drain the bag into the toilet without having to remove the bag from the patient's body.

U.S. Pat. No. 6,045,097 to Gaffar discloses a dialysis bag holder, the construction of which is intended to fill the bag, rather than drain same.

While the available units may be suitable for the particular purpose employed, or for general use, they would not be as suitable for the purposes of the present invention as disclosed hereafter.

SUMMARY OF THE INVENTION

In the view of the foregoing disadvantages inherent in the prior art, the present invention provides an improved peritoneal waste bag support and drainage device. As such, the general purpose of the present invention, which will be described subsequently in greater detail, is to provide a new and improved peritoneal waste bag support and drainage device which has all the advantages of the prior art and none of the disadvantages.

To attain this, the present invention essentially comprises a peritoneal waste bag support and drainage device having a pair of front legs, a pair of rear legs, and a flat horizontal table supported by the front and rear legs. The table has a front end, a rear end, a top surface, and a bottom surface. Each pair of legs has a main portion and a bottom sleeve. The main portion extends downward from the bottom surface of the table, while the bottom sleeve extends upward from the ground and envelopes the main portion of the legs. In order to adjust the length of the legs, the main portion is slid inside the corresponding bottom sleeve until the desired height is reached. When setting up the support device for use, in order to facilitate flow of fluid from a peritoneal waste bag, the front legs should be adjusted to a shorter height than the rear legs. Further, the device is collapsible in order to allow it be stored beside a toilet when not in use, or carried to various destinations when traveling.

There has thus been outlined, rather broadly, the more important features of the invention in order that the detailed description thereof that follows may be better understood, and in order that the present contribution to the art may be better appreciated. There are, of course, additional features of the invention that will be described hereinafter and which will form the subject matter of the claims appended hereto.

In this respect, before explaining at least one embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of description and should not be regarded as limiting.

As such, those skilled in the art will appreciate that the conception, upon which this disclosure is based, may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

It is therefore an object of the present invention to provide a new and improved peritoneal waste bag support and drainage device which has all the advantages of the prior art and none of the disadvantages.

It is another object of the present invention to provide a new and improved peritoneal waste bag support and drainage device which may be easily and efficiently manufactured and marketed.

It is a further object of the present invention to provide a new and improved peritoneal waste bag support and drainage device which is of durable and reliable construction.

An even further object of the present invention is to provide a new and improved peritoneal waste bag support and drainage device which is susceptible of a low cost of manufacture with regard to both materials and labor, and which accordingly is then susceptible of low prices of sale to the consuming public, thereby making such peritoneal waste bag draining device economically available to the buying public.

An even further object of the present invention is to provide a new and improved peritoneal waste bag support and drainage device which is collapsible into a thin lightweight structure. This feature allows one to conveniently store the support device out of sight. Further, it may easily be transported to additional locations whenever necessary.

These together with other objects of the invention, along with the various features of novelty which characterize the invention, are pointed out with particularity in the claims annexed to and forming a part of this disclosure. For a better understanding of the invention, its operating advantages and the specific objects attained by its uses, reference should be had to the accompanying drawings and descriptive matter in which there is illustrated preferred embodiments of the invention.

To the accomplishment of the above and related objects the invention may be embodied in the form illustrated in the accompanying drawings. Attention is called to the fact, however, that the drawings are illustrative only. Variations are contemplated as being part of the invention, limited only by the scope of the claims.

BRIEF DESCRIPTION OF THE DRAWINGS

In the drawings, like elements are depicted by like reference numerals. The drawings are briefly described as follows.

DETAILED DESCRIPTION OF THE PREFERRED EMBODIMENTS

Figure 1:
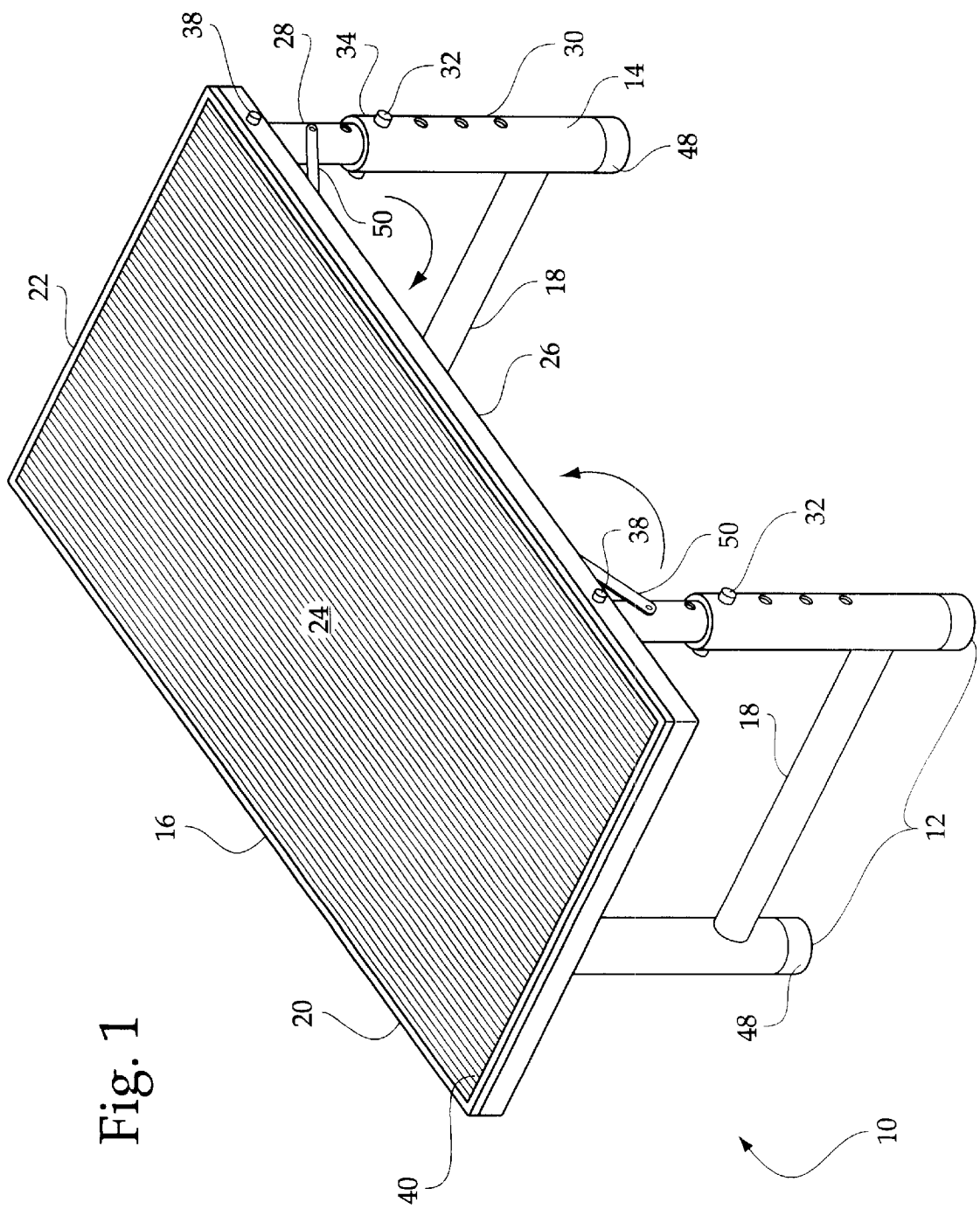
FIG. 1 is a perspective view of the peritoneal waste bag support and drainage device.

FIG. 1 is a perspective view, illustrating a peritoneal waste bag support and drainage device 10, comprising a pair of front legs 12, a pair of rear legs 14, and a flat horizontal table 16 extending over the front and rear legs 12, 14. The table 16 has a front end 20, a rear end 22, a top surface 24, and a bottom surface 26.

Each pair of legs 12, 14 has a main portion 28 and a bottom sleeve 30. By altering the depth that the main portion 28 extends into the bottom sleeve 30, the height of the legs 12, 14 is adjustable in order to alter the distance of the table 16 from a ground surface. The main portion 28 is attached to and extends downward from the bottom surface 26 of the table 16, while the bottom sleeve 30 extends upward from the ground and envelopes the main portion 28 of the legs 12, 14. The diameter of the bottom sleeve 30 is slightly larger than that of the main portion 28 in order to accommodate same. A plurality of apertures 34 are situated along the length of the main portions 28 and the bottom sleeves 30. In order to adjust the length of the legs 12, 14, the main portion 28 is slid inside the corresponding bottom sleeve 30 until the desired height is reached. A pin 32 is then inserted through the appropriate aperture 32 in the bottom sleeve 30, and through the corresponding aperture 32 in the main portion 28. A rubber cap 48 covers the base of the bottom sleeve 30 in order to prevent damage to the ground surface. Thus, when setting up the support device 10 for use, the height of the table 16 may be adjusted by altering the length of each pair of legs 12, 14. In order to facilitate drainage from a peritoneal waste bag 44, the front legs 12 may be adjusted to a shorter height than the rear legs 14, causing the table 16 to slant downward toward the front end 20, as seen in FIG. 2.

Figure 3:
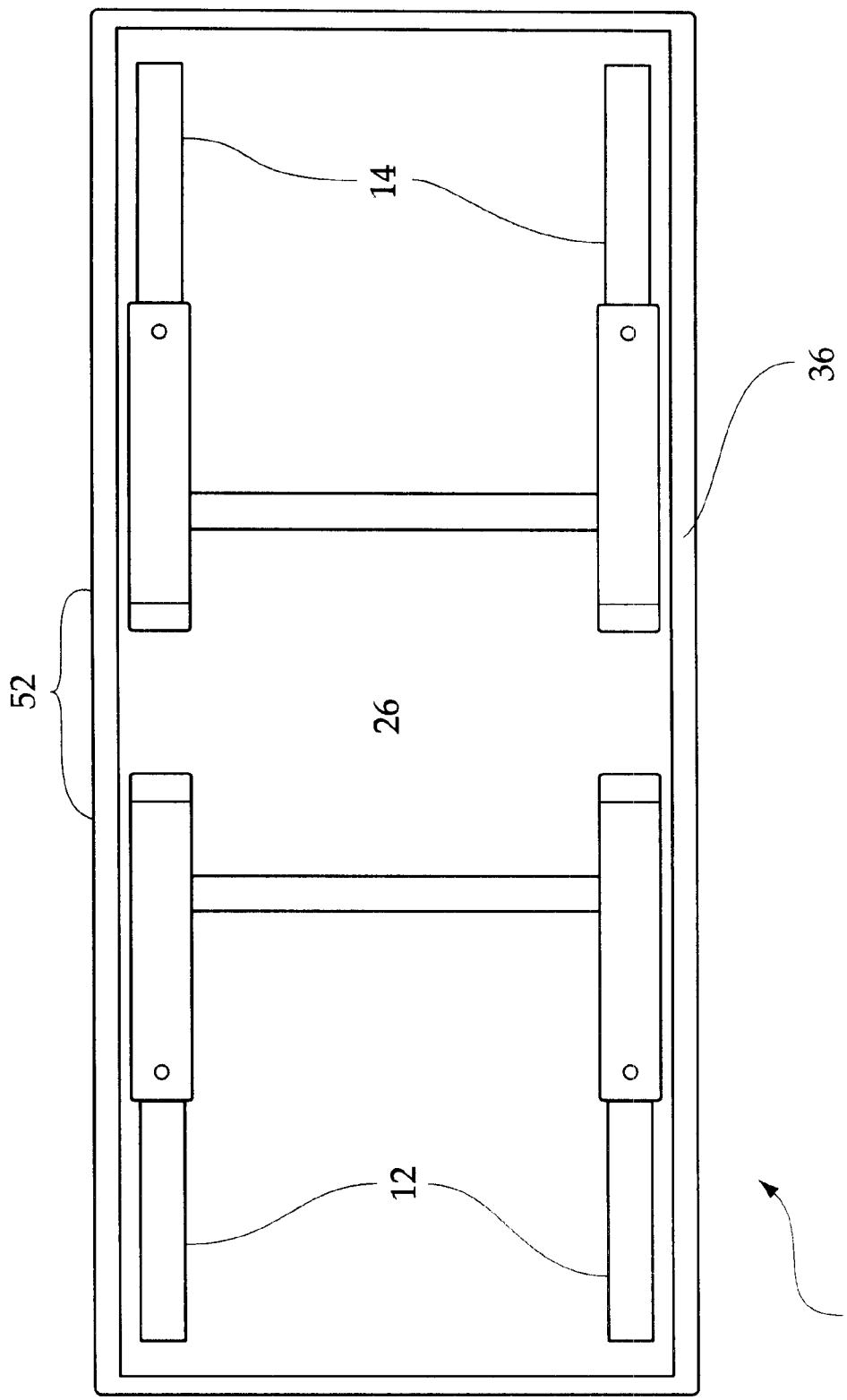
FIG. 3 is a bottom view of the peritoneal waste bag draining device in the collapsed position, ready for storage or transport.

Each pair of legs 12, 14 has a crossbar 18 extending horizontally therebetween. This crossbar 18 lends support to the legs, and ultimately the entire device 10. The crossbar 18 maintains the front legs 12 at the same height, and the rear legs 14 at the same height. Further, a diagonal bracket 50 runs from the main portion 28 of each leg 12, 14 to the bottom surface 36 of the table 16. These brackets 50 allow the legs 12, 14 to collapse under the table 16 in a manner similar to conventional folding tables, as illustrated in FIG. 3. The legs 12, 14 thus folded are then flush with the bottom surface 26 of the table 16, creating an even surface and compact profile. This configuration allows the support device 10 to be easily stored beside a toilet 42 when not in use.

The table 16 extends from the rear legs 14 to a point past the front legs 12. A rim 36 extends downward around the entire perimeter of the table 16. This rim 36 is attached to each leg 12, 14 by means of a fastener 38, namely a bolt. An overhang 40 is defined as the region of the table 16 which extends beyond the pair of front legs 12. The top surface 24 of the table 16 is coated with a rubber non-skid material in order to prevent a peritoneal waste bag 44 resting thereon from slipping. Further, a handle 52 may be positioned on the rim 36 in order to allow the device to be easily carried.

Figure 2:
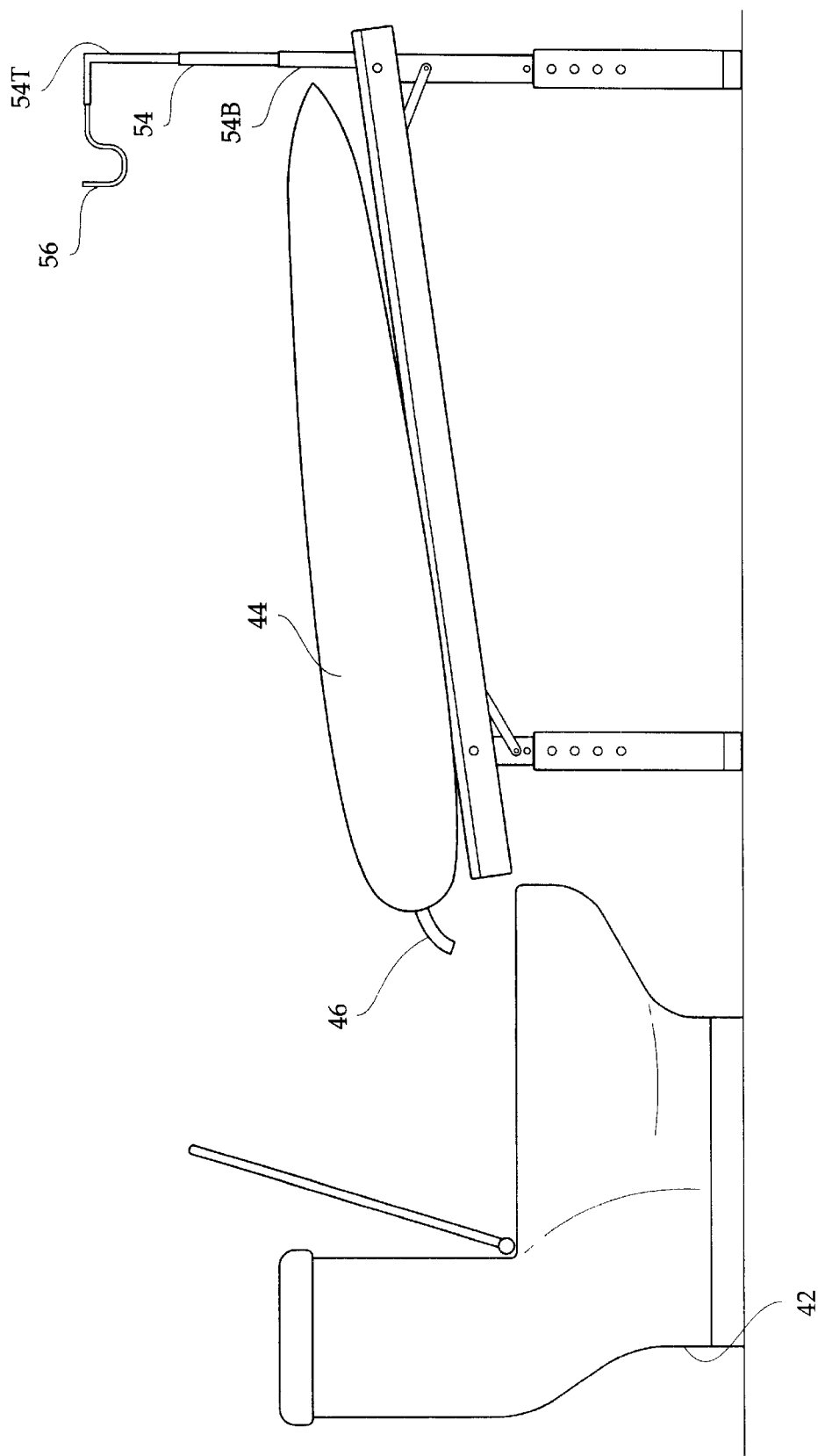
FIG. 2 is a perspective view of the peritoneal waste bag support and drainage device in use next to a toilet, wherein one side of the table has been lowered to accomplish draining of the peritoneal waste bag.

In order to drain the peritoneal waste bag 44, the support device 10 is placed in front of a toilet 42, as illustrated in FIG. 2, wherein the front legs 12 are positioned adjacent to said toilet 42, and adjusted to a shorter height than the rear legs 14, lowering the front end of the table 16 with respect to the rear end thereof. The overhang 40 is thereby situated in the space between the device 10 and the toilet 42 in order to avoid any spillage when draining one's peritoneal waste bag 44. The peritoneal waste bag 44 has a plug 46 for drainage. The bag 44 is placed on the top surface 24 of the table 16, with the plug 46 situated at the overhang 40. The plug 46 is then removed from the bag 44, thereby allowing the waste stored therein to drain into the toilet 42. Once emptied, the bag 44 is removed and the support device 10 may be folded for storage.

As an addition to the peritoneal waste bag draining device 10, a vertical extension 54 may be attached near the rear end 22 of the table 16, telescoping upward to extend significantly above the table 16. The extension 54 has a top end 54T and a bottom end 54B. A hook 56 is attached to the top end 54T and serves to elevate the waste bag 44 for drainage. After use, the extension 54 would telescope into the hollow interior of one of the rear legs 14 for storage.

In conclusion, herein is presented a peritoneal waste bag support and drainage device for facilitating easy drainage of the bag into a toilet. The invention is illustrated by example in the drawing figures, and throughout the written description. It should be understood that numerous variations are possible, while adhering to the inventive concept. Such variations are contemplated as being a part of the present invention.

What is claimed is:

1. A method of utilizing a peritoneal waste bag support and drainage device for supporting a waste bag having a plug during drainage of said bag into a toilet, said device having a pair of front legs, and a table extending over the front legs, the table having a top surface, a bottom surface, a front end, a rear end, and an overhang extending from the front end to a point past the front legs, comprising the steps of:

slanting the table downward toward the front legs;

positioning the support device adjacent to a toilet, with the front legs closest to the toilet and the overhang substantially touching the toilet;

placing the waste bag on the top surface of the table with the plug positioned on the overhang of the table; and removing the plug and allowing the waste to drain into the toilet.

\* \* \* \* \*